(12) United States Patent
Loftman et al.

(10) Patent No.: US 6,589,182 B1
(45) Date of Patent: Jul. 8, 2003

(54) MEDICAL DIAGNOSTIC ULTRASOUND CATHETER WITH FIRST AND SECOND TIP PORTIONS

(75) Inventors: Rickard C. Loftman, Mountain View, CA (US); Randall L. Schlesinger, San Mateo, CA (US); John I. Jackson, Menlo Park, CA (US); Lex J. Garbini, San Gregorio, CA (US); Douglas B. Dull, Palo Alto, CA (US)

(73) Assignee: Acuson Corporation, Mountain View, CA (US)

( * ) Notice: Subject to any disclaimer, the term of this patent is extended or adjusted under 35 U.S.C. 154(b) by 183 days.

(21) Appl. No.: 09/781,694

(22) Filed: Feb. 12, 2001

(51) Int. Cl.⁷ .............................. A61B 8/00; A61B 8/12
(52) U.S. Cl. ....................................... 600/466; 600/463
(58) Field of Search ................................. 600/466, 472, 600/459, 463

(56) References Cited

U.S. PATENT DOCUMENTS

| | | |
|---|---|---|
| 3,927,675 A | 12/1975 | Pohlman et al. |
| 4,637,401 A | 1/1987 | Johnston |
| 4,674,336 A | 6/1987 | Johnston |
| 4,802,490 A | 2/1989 | Johnston |
| 5,106,377 A | 4/1992 | Martin |
| 5,152,293 A | 10/1992 | Vonesh et al. |
| 5,267,954 A | 12/1993 | Nita |
| 5,297,553 A | 3/1994 | Sliwa, Jr. et al. |
| 5,312,328 A | 5/1994 | Nita et al. |
| 5,344,435 A | 9/1994 | Turner et al. |
| 5,368,037 A | 11/1994 | Eberle et al. |
| 5,382,228 A | 1/1995 | Nita et al. |
| 5,405,318 A | 4/1995 | Nita |
| 5,480,379 A | 1/1996 | La Rosa |
| 5,586,982 A | 12/1996 | Abela |
| 5,588,432 A | 12/1996 | Crowley |
| 5,603,327 A | 2/1997 | Eberle et al. |
| 5,749,914 A | 5/1998 | Janssen |
| 5,779,644 A | 7/1998 | Eberle et al. |
| 5,795,229 A | 8/1998 | Eaton et al. |
| 5,797,848 A | * 8/1998 | Marian et al. ............... 600/459 |
| 5,840,031 A | 11/1998 | Crowley |
| 5,846,205 A | * 12/1998 | Curley et al. ............... 600/472 |
| 5,891,133 A | 4/1999 | Murphy-Chutorian |
| 5,916,170 A | 6/1999 | Kolz et al. |
| 5,935,075 A | 8/1999 | Casscells et al. |
| 5,938,615 A | 8/1999 | Eberle et al. |
| 5,938,616 A | * 8/1999 | Eaton et al. ................. 600/463 |
| 5,954,654 A | 9/1999 | Eaton et al. |
| 5,984,871 A | 11/1999 | TenHoff et al. |
| 6,004,269 A | 12/1999 | Crowley et al. |
| 6,024,703 A | 2/2000 | Zanelli et al. |
| 6,027,450 A | 2/2000 | Brown et al. |
| 6,071,276 A | 6/2000 | Abela |
| 6,149,599 A | * 11/2000 | Schlesinger et al. ........ 600/472 |

OTHER PUBLICATIONS

"Ultrasonic Transducer Assembly Controller," U.S. patent application Ser. No. 09/434,594, filed Nov. 5, 1999; inventors: William J. Park, Douglas B. Dull, John W. Eaton, Robert A. Howard, Stephen L. Ijams, Richard W. Henderson, Jeff Gamelsky, Glenn Hansen, and Gill Wong.

"Medical Diagnostic Ultrasound Catheter with Dielectric Isolation," U.S. patent application Ser. No. 09/401,632, filed Sep. 22, 1999; inventors: Randall L. Schlesinger and Mathew Rahimi.

* cited by examiner

*Primary Examiner*—Marvin M. Lateef
*Assistant Examiner*—Ruby Jain

(57) ABSTRACT

The preferred embodiments described herein provide a medical diagnostic ultrasound catheter with a tip portion carrying an ultrasound transducer. The tip portion comprises a first portion that is in the acoustic path of the ultrasound transducer, and a second portion that is outside the acoustic path of the ultrasound transducer. The first and second portions comprise different acoustic and mechanical properties. For example, the mechanical properties of the second portion can give the catheter tip sufficient durability to withstand normal use without bowing, while the acoustic properties of the first portion can give the catheter tip desired acoustic properties. This may be especially important for small diameter catheters (e.g., maximum cross-sectional dimensions less than or equal to about 10 French or 8 French) where the stiffness of the catheter tip is reduced.

28 Claims, 3 Drawing Sheets

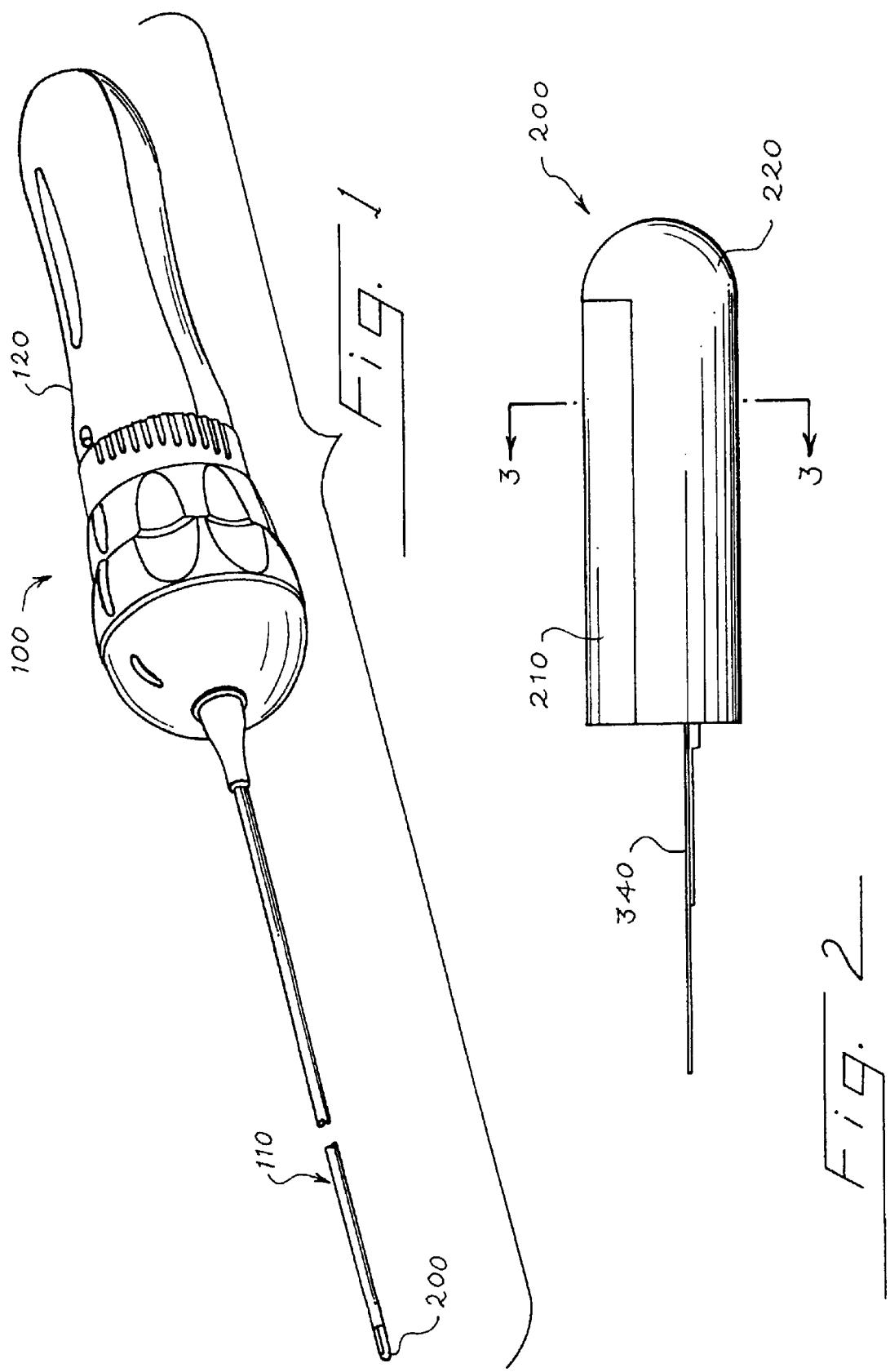

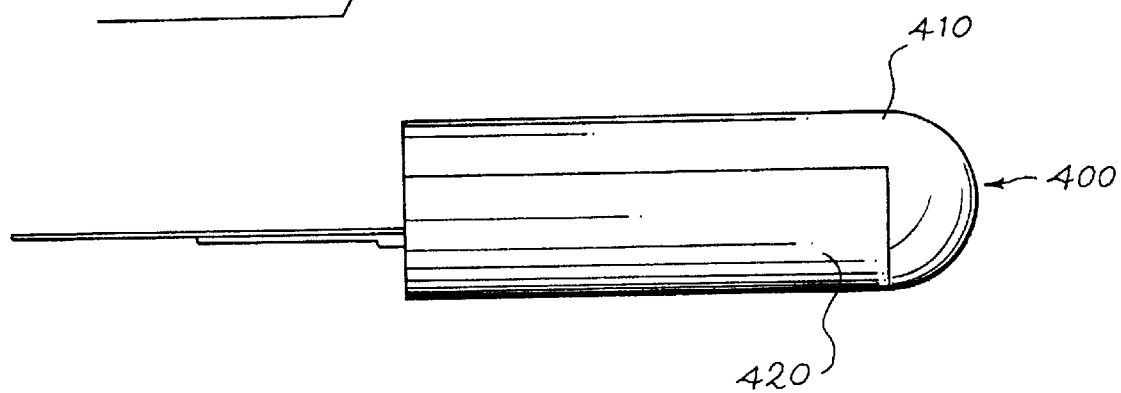
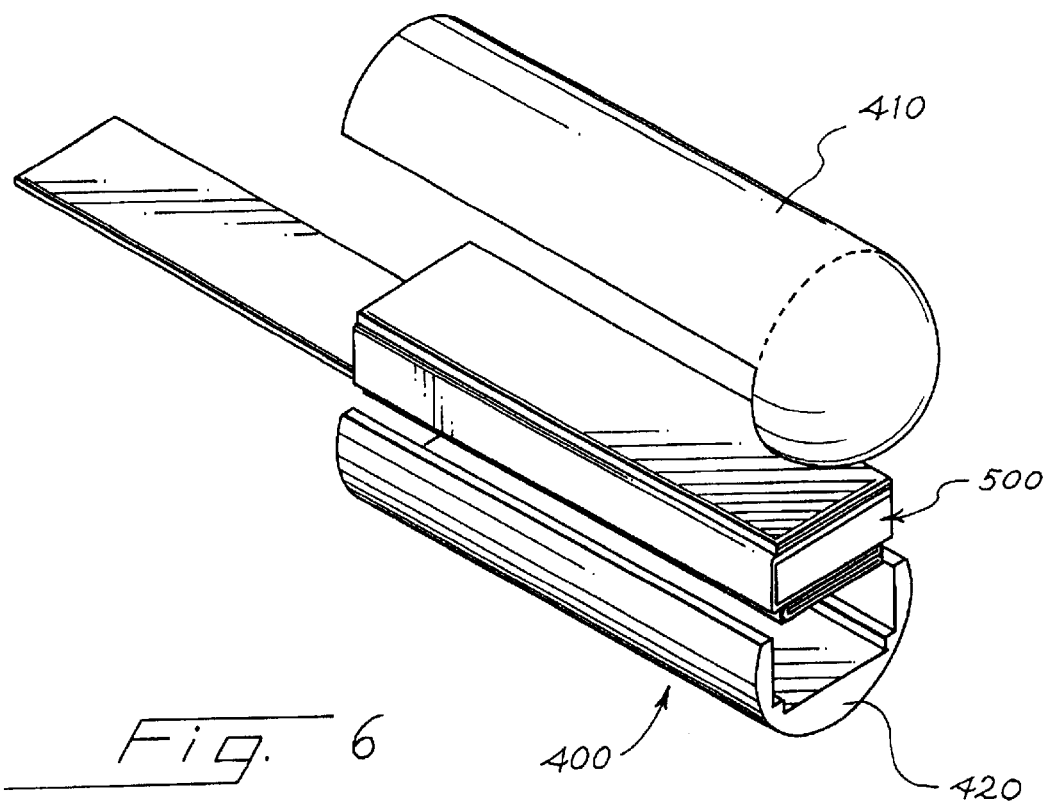

MEDICAL DIAGNOSTIC ULTRASOUND CATHETER WITH FIRST AND SECOND TIP PORTIONS

BACKGROUND

Medical diagnostic ultrasound catheters include a shaft portion and a tip portion that surrounds an ultrasound transducer. Such catheters can be used for insertion into the arterial or venous system for imaging of blood flow or the heart. The tip portion of the ultrasound catheter is typically a homogeneous material that is selected for its acoustic properties. For example, a plastic that conducts ultrasound waves at a speed near that to the speed of sound in tissue or blood is often used. Although the material used for the tip portion may possess the desired acoustic characteristics, it may be relatively mechanically weak. For many catheters, though, the backing block material of the ultrasound transducer assembly aides in providing mechanical stability. However, when the diameter of a catheter is reduced, it is often necessary to thin the backing block material. For example, in moving from 10 French to 8 French, the backing block may be reduced from 30 mils to 20 mils. This reduction in the backing block reduces the mechanical stability of the catheter tip and can lead to de-lamination of the tip material from the transducer assembly. While using a tip material having greater mechanical strength avoids this problem, such a tip material may not provide desired acoustic properties.

There is a need, therefore, for a medical diagnostic ultrasound catheter that overcomes the problems described above.

SUMMARY

The present invention is defined by the following claims, and nothing in this section should be taken as a limitation on those claims.

By way of introduction, the preferred embodiments described below provide a medical diagnostic ultrasound catheter with a tip portion carrying an ultrasound transducer. The tip portion comprises a first portion that is in the acoustic path of the ultrasound transducer, and a second portion that is outside the acoustic path of the ultrasound transducer. The first and second portions comprise different acoustic and mechanical properties. For example, the mechanical properties of the second portion can give the catheter tip sufficient durability to withstand normal use without bowing, while the acoustic properties of the first portion can give the catheter tip desired acoustic properties. This may be especially important for small diameter catheters (e.g., maximum cross-sectional dimensions less than or equal to about 10 French or 8 French) where the stiffness of the catheter tip is reduced.

The preferred embodiments will now be described with reference to the attached drawings.

BRIEF DESCRIPTION OF THE DRAWINGS

FIG. 1 is an illustration of a medical diagnostic ultrasound catheter of a preferred embodiment.

FIG. 2 is an illustration of a medical diagnostic ultrasound catheter tip portion of a preferred embodiment.

FIG. 5 is an illustration of a medical diagnostic ultrasound catheter tip portion of another preferred embodiment.

FIG. 6 is an exploded view of the medical diagnostic ultrasound catheter tip portion of FIG. 5.

DETAILED DESCRIPTION OF THE PRESENTLY PREFERRED EMBODIMENTS

Turning now to the drawings, FIG. 1 is an illustration of a medical diagnostic ultrasound catheter 100 of a preferred embodiment. As shown in FIG. 1, this catheter 100 comprises a shaft portion 110 that is coupled to a controller section 120 at its proximal end. As used herein, the term "coupled with" means directly coupled with or indirectly coupled with through one or more components. A suitable controller is described in U.S. patent application Ser. No. 09/434,594, which is assigned to the assignee of the present invention and is hereby incorporated by reference. The catheter 100 also comprises a tip portion 200 at its distal end. In one preferred embodiment, the shaft portion 110 is about 100 centimeters long, and the tip portion 200 is about 400 mils long. Of course, the length and diameter of the shaft portion 110 and the tip portion 200 can be adapted for any particular application.

Figure 3:
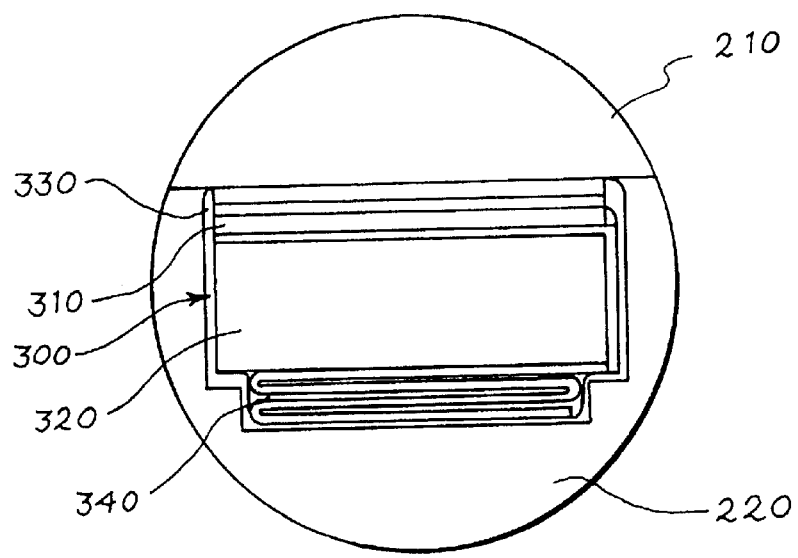
FIG. 3 is a cross-sectional view of the medical diagnostic ultrasound catheter tip portion of FIG. 2 taken along line 3—3.
Figure 4:
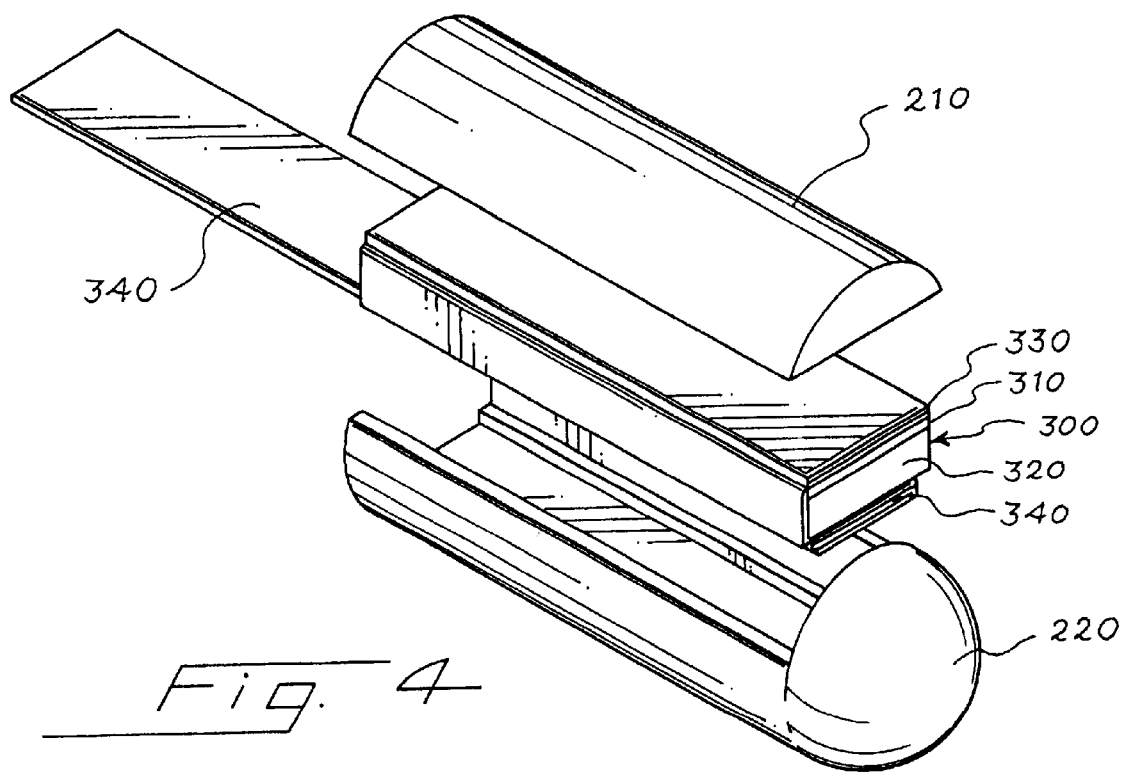
FIG. 4 is an exploded view of the medical diagnostic ultrasound catheter tip portion of FIG. 2.

FIG. 2 shows the tip portion 200 in more detail. As shown in FIG. 2, the tip portion 200 comprises a first portion 210 and a second portion 220, both of which will be described in more detail below. FIG. 3 shows a cross-sectional view of the tip portion 200, and FIG. 4 shows an exploded view of the tip portion 200. As shown in these figures, the tip portion 200 carries an ultrasound transducer 300, which, in this preferred embodiment, is a side-firing phased-array transducer (i.e., the ultrasound transducer 300 defines an azimuthal axis that is parallel to the longitudinal axis of the catheter tip portion 200). Other transducers (e.g., a single-element transducer) and firing arrangements (e.g., front-firing) can be used.

The ultrasound transducer 300 of this preferred embodiment comprises a piezoelectric material (such as PZT) 310 formed into individual elements, arranged side by side with the lengths of individual elements parallel to one another. The PZT 310 is built on a backing material 320 that reflects most of the ultrasound energy generated by the PZT 310 and also tends to absorb energy that is coupled into it. The backing material 320 can be formed as described in U.S. Pat. No. 5,297,553, which is assigned to the assignee of the present invention and is hereby incorporated by reference. The active surface of the PZT 310 is covered with a matching layer 330, which couples ultrasonic energy from the PZT 310 into the tissue that the transducer 300 is in contact with. The backing material 320 and the matching layer 330 are typically made of composite material such as epoxy loaded with a heavier material such as alumina.

As shown in FIGS. 3 and 4, the ultrasound transducer assembly 300 also comprises a flexible circuit 340. The flexible circuit 340 applies voltages sent from a transmit beamformer of a diagnostic medical ultrasound imaging system (not shown) to cause the transducer 300 to emit an ultrasonic beam. The flexible circuit 340 also sends voltages representative of reflected ultrasonic energy impinging on the transducer 300 to a receive beamformer of the ultrasound system. A suitable flexible circuit is described in U.S. Pat. No. 5,795,299, which is assigned to the assignee of the present invention and is hereby incorporated by reference. The transducer stack 300 and the portion of the flexible circuit 340 underneath the transducer stack 300 can be wrapped with a thin dielectric material to keep the flexible circuit 340 bundled together with the transducer stack 300 and to provide electrical insulation. A suitable dielectric material is described in U.S. patent application Ser. No. 09/401,632, which is assigned to the assignee of the present invention and is hereby incorporated by reference.

The active surface of the ultrasound transducer 300 defines an acoustic path along which the ultrasound transducer 300 transmits and receives ultrasonic waves. As shown in FIG. 4, the first portion 210 of the catheter tip 200 is in the acoustic path of the ultrasound transducer 300, and the second portion 220 of the catheter tip 200 is outside the acoustic path of the ultrasound transducer 300. The first and second portions 210, 220 comprise different acoustic and mechanical properties. For example, to provide the catheter tip 200 with good imaging performance and good mechanical properties for insertion and use of the catheter in the body, the first portion 210 can be made of a material having good acoustic performance, and the second portion 220 can be made of durable material. In one presently preferred embodiment, the first portion 210 is made of Pebax 35D, and the second portion is made of Pebax 40D. Pebax 35D and Pebax 40D, which are also known as Pebax 3533 and Pebax 4033, can be obtained from Elf Autochem. Of course, other materials or classes of material can be used.

In one preferred embodiment, the first and second portions 210, 220 conduct ultrasound waves at different speeds. Specifically, the first portion 210 conducts ultrasound waves at a speed more closely matched to a speed of sound in the object being imaged (e.g., tissue or blood) than the second portion 220. It has been found that a material that conducts ultrasound waves at a speed of sound in water provides a good acoustic match when imaging under blood. Pebax 35D, which conducts ultrasound waves at a speed of approximately 1565 m/s, is close to the velocity of water of 1520 m/s and is, therefore, preferred when imaging under blood. The first and second portions 210, 220 can also have different acoustical impedances.

If a material chosen for its desirable acoustic properties were used for both the first and second portions 210, 220, the tip 200 may not have acceptable mechanical properties. Accordingly, it is preferred that the second portion 220 have a greater mechanical strength (e.g., higher durometer) than the first portion. It is preferred that Pebax 40D be used for the second portion 220. If the material chosen for its desirable mechanical strength properties were used for both the first and second portions 210, 220, the tip 200 may not have acceptable acoustic properties. For example, Pebax 40D conducts ultrasound waves at a speed of approximately 1744 m/s. If Pebax 40D were used for both the first and second portions 210, 220, the tip 200 would have suitable mechanical properties but would not have desired acoustic properties. Accordingly, in this preferred embodiment, the first portion 210 is made of Pebax 35D (for its acoustic properties), and the second portion 220 is made of Pebax 40D (for its mechanical properties). While the first and second portions 210, 220 are different classes of the same material in this embodiment, the first and second portions 210, 220 can comprise different materials. However, by using different classes of the same material, the first and second portions 210, 220 can be fused together by thermal heating, as described below. Further, if the material used for the catheter tip 200 is the same as the material used for the shaft portion 110, the catheter tip portion 200 and the shaft portion 110 can be fused together. If separate materials are used, the first and second portions 210, 220 can be joined together using an adhesive.

There are several advantages associated with these preferred embodiments. The mechanical properties of the second portion 220 give the catheter tip 200 sufficient durability to withstand normal use without bowing and without degrading imaging performance, while the acoustic properties of the first portion 210 give the catheter tip 200 desired acoustic properties without degrading mechanical performance. This may be especially important for smaller-diameter catheters (e.g., maximum cross-sectional dimension less than or equal to about 10 French or 8 French) where the thickness of the backing block is reduced. Of course, the benefits of these preferred embodiment can be received with any size catheter tip, and the invention is not restricted to the sizes mentioned above unless specifically recited in the claims. Additionally, because it is constructed with separate regions of distinct material properties, the catheter tip of these preferred embodiments avoids the compromise between mechanical and acoustic properties required by the homogeneous catheter tip of the prior art.

There are several alternatives that can be employed with these preferred embodiments. For example, designs other than the ones described above can be used to provide desired acoustical and mechanical properties for the catheter tip. In the preferred embodiment described above, the first portion 210 was in the acoustic path of the ultrasound transducer 300 (and not outside of the acoustic path), and the second portion 220 was outside the acoustic path of the ultrasound transducer 300 (and not in the acoustic path). In an alternate embodiment shown in FIGS. 5 and 6, part of the first portion 410 of the catheter tip 400 is in the acoustic path of the ultrasound transducer 500, while another part of the first portion 410 is outside the acoustic path of the ultrasound transducer 500. Unlike the embodiment shown in FIG. 4 where part of the second portion is located at the distal end of the tip portion, in the embodiment shown in FIGS. 5 and 6, part of the first portion is located at the distal end of the tip portion. Similarly, in another alternate embodiment, part of the second portion can be in the acoustic path of the ultrasound transducer. Further, while the first portion in the preferred embodiment described above conducted ultrasound waves at a speed equal to about the speed of sound in tissue or blood, in another alternate embodiment, the first portion conducts ultrasound waves at greater or lesser speeds to adjust the elevational beam pattern to improve imaging resolution in the out-of-plane dimension. For example, if the first portion conducts ultrasound waves at a speed of sound less than the speed of sound in blood, focusing along the elevation direction can be improved. Additionally, although the first portion can be referred to as an acoustic window because it is in the acoustic path of the transducer, it should be noted that the material for the first portion can be chosen to obtain focusing, defocusing, and non-focusing characteristics.

While the catheter tip in the preferred embodiment described above was made from two separate portions, a single-piece catheter tip with portions having different characteristics can be used, such as when the catheter tip is cast all at once with materials having different characteristics. Additionally, while the first portion is shown as a single component, the first portion can be made up of two or more individual components. In another embodiment, at least some part of the first portion is visually discernable from the second portion to allow a physician to know where the ultrasound transducer is in the catheter tip. For example, at least some part of the first portion can be a different color from the second portion. In yet another embodiment, the shape of the first portion is different from the shape of the second portion. For example, the first portion can have a different radius of curvature than the second portion, or the first portion can be flat while the second portion is curved. Providing the first portion with a different shape can provide different focusing characteristics.

The catheter tip can be made using any suitable method. In one preferred embodiment, a charge of either the window material or the mechanical material is placed inside a glass tube with the inner diameter of the glass tube being the same size as the outer diameter of the finished catheter. A distal tip die is placed in one end of the glass tube with another insert die placed in the other end of the glass tube. The piece being formed is governed by the length of the glass tube and features on the die that reference off the end of the glass tube. The piece being made is also the reverse shape of the insert die. Thus, if the window portion is being made, the insert die would be the shape of the mechanical portion of the tip and the transducer stack assembly. If the mechanical portion of the tip is being made, the insert die would be the shape of the window portion and the transducer stack assembly. The die assembly and glass tube are heated locally where the charge is, and as the charge gets close to melting or partially melts, the dies are forced inward, and the material forms around the dies. As the material is cooled, pressure is kept on the dies, and the dies are pushed close to mechanical stop of the ends of the glass tube. This helps in eliminating voiding. After cooling, the dies are pulled out of the glass tube. The formed part either is attached to the insert die and is removed from the insert die, or the formed part remains in the glass tube and is then pulled out. This process is repeated for either the window portion or the mechanical portion using the appropriate insert die and appropriate material. In an alternate method, the window portion and/or the mechanical portion is extruded to the appropriate shape.

Once both the window portion and the mechanical portion are formed, the pieces may be used with the transducer stack assembly to create the tip of the catheter that is fused to the main catheter shaft. The main catheter shaft is stuffed with the flexible circuit bundle, and the flexible circuit bundle on the distal end is attached to the transducer stack assembly. The stack itself and the flexible circuit bundle underneath the stack may be wrapped with a thin dielectric material to keep the flexible circuit bundle together with the stack and to provide electrical insulation. The two tip portions may need to be cut to the proper length if they are not formed to the proper length. The pieces sandwich the transducer stack assembly with the window portion at the face of the transducer stack assembly. The sandwich with the transducer stack assembly may be placed in the middle of the glass tube with inner diameter of the glass tube the same as the outer diameter of the finished catheter. The main catheter shaft is butted up to the edge of the sandwich inside the glass tube. Pulling the flex bundle from the proximal end or sliding the main catheter over the flex bundle may do this. Once the tip is butted to the catheter, the distal tip die may be inserted into the glass tube from the distal end. The glass tube assembly is ready for localized heating such as a hot air knife to thermally melt the tip. Using a profile of time, temperature, and location, the materials are re-flowed and fused between the two plastic material pieces and transducer stack assembly and fused together as a butt weld to the main catheter shaft. The glass tube assembly with the fused tip is cooled to room temperature and the fused tip is removed from the glass. In one embodiment, the first portion and/or the second portion has serrated joining edges to improve the bond between the first and second portions.

It is intended that the foregoing detailed description be understood as an illustration of selected forms that the invention can take and not as a definition of the invention. It is only the following claims, including all equivalents, that are intended to define the scope of this invention.

What is claimed is:

1. A medical diagnostic ultrasound catheter comprising:
   an ultrasound transducer; and
   a catheter comprising a tip portion carrying the ultrasound transducer, the tip portion comprising a first portion in an acoustic path of the ultrasound transducer and a second portion outside the acoustic path of the ultrasound transducer, wherein the first and second portions comprise different acoustic and mechanical properties.

2. A medical diagnostic ultrasound catheter tip portion shaped to carry an ultrasound transducer, the tip portion comprising:
   a first portion in an acoustic path of an ultrasound transducer carried by the tip portion; and
   a second portion outside the acoustic path of the ultrasound transducer carried by the tip portion, wherein the first and second portions comprise different acoustic and mechanical properties.

3. The invention of claim 1 or 2, wherein the first and second portions conduct ultrasound waves at different speeds.

4. The invention of claim 3, wherein the first portion conducts ultrasound waves at a speed more closely matched to a speed of sound in blood than the second portion.

5. The invention of claim 3, wherein the first portion conducts ultrasound waves at a speed matched to a speed of sound in blood.

6. The invention of claim 3, wherein the first portion conducts ultrasound waves at a speed of about 1565 m/s.

7. The invention of claim 3, wherein the first portion conducts ultrasound waves at a speed of about 1520 m/s.

8. The invention of claim 1 or 2, wherein the first portion conducts ultrasound waves at a speed of sound less than a speed of sound in blood.

9. The invention of claim 1 or 2, wherein the second portion has a greater mechanical strength than the first portion.

10. The invention of claim 1 or 2, wherein the second portion comprises a higher durometer than the first portion.

11. The invention of claim 1 or 2, wherein the first and second portions comprise different materials.

12. The invention of claim 1 or 2, wherein the first and second portions comprise different classes of a same material.

13. The invention of claim 1 or 2, wherein the first portion comprises Pebax 35D.

14. The invention of claim 1 or 2, wherein the second portion comprises Pebax 40D.

15. The invention of claim 1 or 2, wherein the first portion and the second portion are fused together.

16. The invention of claim 1 or 2, wherein the first portion and the second portion are adhered together.

17. The invention of claim 1 or 2, wherein at least one of the first and second portions is molded into shape.

18. The invention of claim 1 or 2, wherein at least one of the first and second portions is extruded.

19. The invention of claim 1 or 2, wherein the tip portion is characterized by a maximum cross-sectional dimension less than or equal to about 10 French.

20. The invention of claim 1 or 2, wherein the tip portion is characterized by a maximum cross-sectional dimension less than or equal to about 8 French.

21. The invention of claim 1 or 2, wherein at least part of the first portion is visually discernable from the second portion.

22. The invention of claim 21, wherein at least part of the first portion is a different color from the second portion.

23. The invention of claim 1 or 2, wherein at least one of the first portion and the second portion comprises a serrated joining edge.

24. The invention of claim 1 or 2, wherein the tip portion comprises a distal end, and wherein at least part of the first portion is located at the distal end.

25. The invention of claim 1 or 2, wherein the tip portion comprises a distal end, and wherein at least part of the second portion is located at the distal end.

26. The invention of claim 1 or 2, wherein the first and second portions comprise different shapes.

27. The invention of claim 1 or 2, wherein the first and second portions comprise different acoustical impedances.

28. The invention of claim 1, wherein the catheter comprises a catheter shaft, and wherein the tip portion is fused with the catheter shaft.

\* \* \* \* \*